United States Patent [19]

Prock

[11] Patent Number: 5,069,202
[45] Date of Patent: Dec. 3, 1991

[54] ANKLE BRACE

[76] Inventor: Steven D. Prock, 120 S. Crockett, Sherman, Tex. 75090

[21] Appl. No.: 609,260

[22] Filed: Nov. 5, 1990

[51] Int. Cl.$^5$ .............................................. A61F 5/00
[52] U.S. Cl. .............................. 128/80 H; 128/80 R; 128/80 F; 128/88
[58] Field of Search ................ 128/80 H, 80 R, 80 E, 128/80 F, 80 S, 87 R, 88, 89 R, 90

[56] References Cited

U.S. PATENT DOCUMENTS

| | | | |
|---|---|---|---|
| 2,952,459 | 9/1960 | Moffitt | 128/80 H |
| 3,064,644 | 11/1962 | Patterson | 128/80 H |
| 3,732,861 | 5/1973 | Lehneis | 128/80 F X |
| 3,805,773 | 4/1974 | Sichau | 128/80 F X |
| 4,050,455 | 9/1977 | Smith | 128/80 F |
| 4,102,337 | 7/1978 | Golia | 128/80 E |
| 4,136,404 | 1/1979 | Lange | 128/80 R X |
| 4,320,748 | 3/1980 | Racette et al. | 128/80 F |
| 4,494,534 | 1/1985 | Hutson | 128/88 X |
| 4,517,968 | 5/1985 | Greene et al. | 128/80 H |
| 4,556,054 | 12/1985 | Paulseth | 128/80 H |
| 4,587,962 | 5/1986 | Greene et al. | 128/80 H |
| 4,665,904 | 5/1987 | Lerman | 128/80 H |
| 4,688,559 | 8/1987 | Vito et al. | 128/80 F |
| 4,753,229 | 6/1988 | Sutherland | 128/80 H |
| 4,922,630 | 5/1990 | Robinson | 128/80 H X |
| 4,962,760 | 10/1990 | Jones | 128/80 F |

FOREIGN PATENT DOCUMENTS

| | | | |
|---|---|---|---|
| 563009 | 5/1931 | Fed. Rep. of Germany | 128/80 H |
| 779873 | 10/1934 | France | 128/80 H |
| 0001659 | 5/1982 | World Int. Prop. O. | 128/80 H |

*Primary Examiner*—Richard J. Apley
*Assistant Examiner*—Linda C. M. Dvorak
*Attorney, Agent, or Firm*—Johnson & Gibbs

[57] ABSTRACT

An ankle brace for therapeutic and preventive treatment of ankle sprains including a foot shell having upright medial and lateral sidewalls and a curved posterior wall, medial and lateral upright members hinged to the sidewalls, an anterior band formed integral with and connected to the upper ends of the upright members for positioning across the tibia crest of a wearer, a leg strap connectable around the leg of a wearer and the anterior band for holding the band against the leg of the wearer, a foot strap connectable between the medial or lateral sidewall near the posterior wall at an angle across the top of the foot of the wearer to a forward portion of the opposite sidewall, and an ankle strap connectable from the same medial or lateral sidewall as the foot strap and around the ankle of a wearer above the medial and lateral melleoli of the wearer and around the opposite upright member. In a preferred form the foot shell, upright members, and anterior band are formed of thin molded plastic and the leg, foot strap, and ankle strap are formed of fabric materials.

24 Claims, 1 Drawing Sheet ized, effective, ankle brace which will properly support the ankle while not unduly limiting its movement

ANKLE BRACE

BACKGROUND OF THE INVENTION

This invention relates generally to orthopedic devices and more particularly to ankle braces for treatment and prevention of ankle sprains.

Generally, there are two types ankle sprains, medial or inside ankle sprains, and lateral or outside ankle sprains. The major portion of such sprains are lateral sprains which result from inversion or a turning in movement of the foot which effects a turning out of the ankle spraining the lateral compartment ligaments, that support the ankle against turning out. A significant portion of injuries, particularly to athletes, are by ankle sprains. It is common practice to wrap sprain ankles with Ace bandages to immobilize the ankle joint. To effectively protect an ankle by taping usually limits the motion of the ankle to the extent that athletes' performances are impaired. Thus, the availability of a light weight, effective, ankle brace which will properly support the ankle while not unduly limiting its movement and the circulation in the leg of the athlete is highly desirable.

A number of different forms of ankle braces have been described and illustrated in prior United States patents.

U.S. Pat. No. 3,073,305 issued Jan. 15, 1963, to Ernest R. Biggs, et al, shows an ankle-brace including a fabric sleeve fitting along the foot and ankle with a strap arrangement spiraling up the leg and essentially vertical stays inserted in pockets along the leg part of the sleeve.

U.S. Pat. No. 4,280,489 issued July 28, 1981, to Glenn W. Johnson, Jr., shows an ankle brace in the form of a U-shaped stirrup including an encircling strap holding the side pieces together around the leg above the ankle.

U.S. Pat. No. 4,378,793 issued Apr. 5, 1983, to Donald M. Mauldin, et al, shows an ankle brace having a laminated foot member, side members, a number of straps up the leg above the ankle, and cross straps along the foot.

U.S. Pat. No. 4,510,927 issued Apr. 16, 1985, to Rick E. Peters, shows an ankle brace having a foot member, a side leg member pivoted at about the ankle level to the foot member, straps encircling the leg above the ankle holding the side member together along the leg, and a cross strap extending from either sides of the foot member over the foot to hold the foot member on the wearer's foot.

U.S. Pat. No. 4,517,968 issued May 21, 1985, to Ted J. Greene, et al., shows an ankle brace having a foot plate with side leg members pivoted to the foot plate and using a spiral elastic bandage holding the side members along the leg.

U.S. Pat. No. 4,523,394 issued June 18, 1985, to Kjel E. Lindh et al, shows an ankle brace having a foot plate, an ankle sleeve, and connecting straps.

U.S. Pat. No. 4,556,054 issued Dec. 3, 1985, to Stephen G. Paulseth, shows an ankle device having a foot plate, a cuff for attachment to the leg above the ankle, and connecting straps.

U.S. Pat. No. 4,665,904 issued May 19, 1987, to Max Lerman, shows an ankle brace having a foot plate with side members and a single strap holding the side members along the leg above the ankle.

U.S. Pat. No. 4,738,252 issued Apr. 19, 1988, to Frank E. Friddle, et al, shows an ankle or leg brace having a foot plate and side members attached by pivoted connections to the foot plate with means for locking the position of the side members relative to the foot plate.

Plate U.S. Pat. No. 4,753,229 issued June 28, 1988, to Tom Sutherland, shows an ankle brace having an ankle cuff and a foot piece interconnected by three straps in an angular arrangement between the foot piece along and outside the leg to the cuff.

U.S. Pat. No. 4,809,686 issued Mar. 7, 1989, to Larry A. Crane, shows an ankle brace made up of a metal assembly which attaches to a shoe and does not use a strap arrangement.

U.S. Pat. No. 4,771,768 issued Sept. 20, 1988, to George E. Crispin, shows an ankle brace having a foot member and side members for either side of the leg pivoted to the foot member by means which allows a fixed angular position of the side members relative to the foot member. Three straps encircling the leg above the ankle and two straps across the foot in front of the ankle are shown.

While the above discussed patented devices provide a number of different approaches to immobilizing an ankle, none are understood to be specifically directed to treating and protecting against lateral and medial sprains, nor do they provide for maximum stabilization of the anterior band used for securing the lateral and medial uprights of the brace to the ankle region.

It is a principal object of the invention to provide a new and improved orthopedic device.

It is another object of the invention to provide a new and improved ankle brace.

It is another object of the invention to provide one form of an ankle brace which particularly protects the lateral compartment ligaments which prevent inversion of the ankle joint.

It is another object of the invention to provide another form of ankle brace which protects the medial compartment ligaments of the wearer.

It is another object of the invention to provide an ankle brace which includes an anterior band providing support and maintaining the lateral spacing of the lateral and medial uprights from the tibia crest.

It is another object of the invention to provide an ankle brace which is simple and lightweight in construction.

It is another object of the invention to provide an ankle brace which may be worn for both protective and therapeutic purposes.

It is another object of the invention to provide an ankle brace which provides maximum protection to ankle using a minimum of straps and other supporting structure.

SUMMARY OF THE INVENTION

In a broader aspect of the invention, an ankle brace is provided for lateral or medial sprains including a foot support shell having lateral and medial sidewalls and a rounded posterior wall, lateral medial uprights pivotally secured to the lateral and medial sidewalls, an anterior band secured with the upper ends of the lateral and medial uprights, a strap secured at one end with one end of the anterior band and adapted to wrap around the posterior portion of the leg of a wearer and secure at the opposite end with the opposite end of the anterior band, a first foot strap secured at a first end with either of the medial or lateral sidewall toward the rear end thereof and extendible across the top of the foot and securable at a second free end with the opposite lateral or medial sidewall toward the front portion thereof, and second ankle strap assembly supported from and spaced above the lateral or medial sidewall inside of the lateral or medial upright above the lateral and the medial melleoli and adapted to be secured around the ankle area of the wearer above the lateral and medial melleoli outside of the opposite medial or lateral upright.

A specific preferred embodiment of the invention includes a foot support shell having a bottom plate, a rounded posterior wall, and lateral and medial sidewalls, lateral and medial upright members hinged at lower ends to the lateral and medial sidewalls, an anterior band connecting and maintaining the lateral spacing of the lateral and medial uprights, an anterior band strap for securing the anterior band along the tibia crest, a foot strap secured at one end to the inside of the medial or lateral sidewall at the posterior wall and connectible across the top of the foot to the opposite lateral or medial sidewall toward the front of the foot, an ankle strap restrainer connected at opposite ends along the inside of the medial or lateral sidewall extending from a central portion of the sidewall upwardly along the adjacent upright and downwardly to the sidewall at the posterior wall, and an ankle strap extending through a loop in the strap restrainer inside of the medial or lateral upright and connectible around the ankle of the wearer above the lateral and medial melleoli, the opposite ends of the ankle strap being secured together outside of the lateral or medial upright.

The foregoing advantages and features of the invention will be readily apparent from the following description of a preferred embodiment of the invention taken in conjunction with the accompanying drawings.

DETAILED DESCRIPTION OF THE INVENTION

Figure 1:
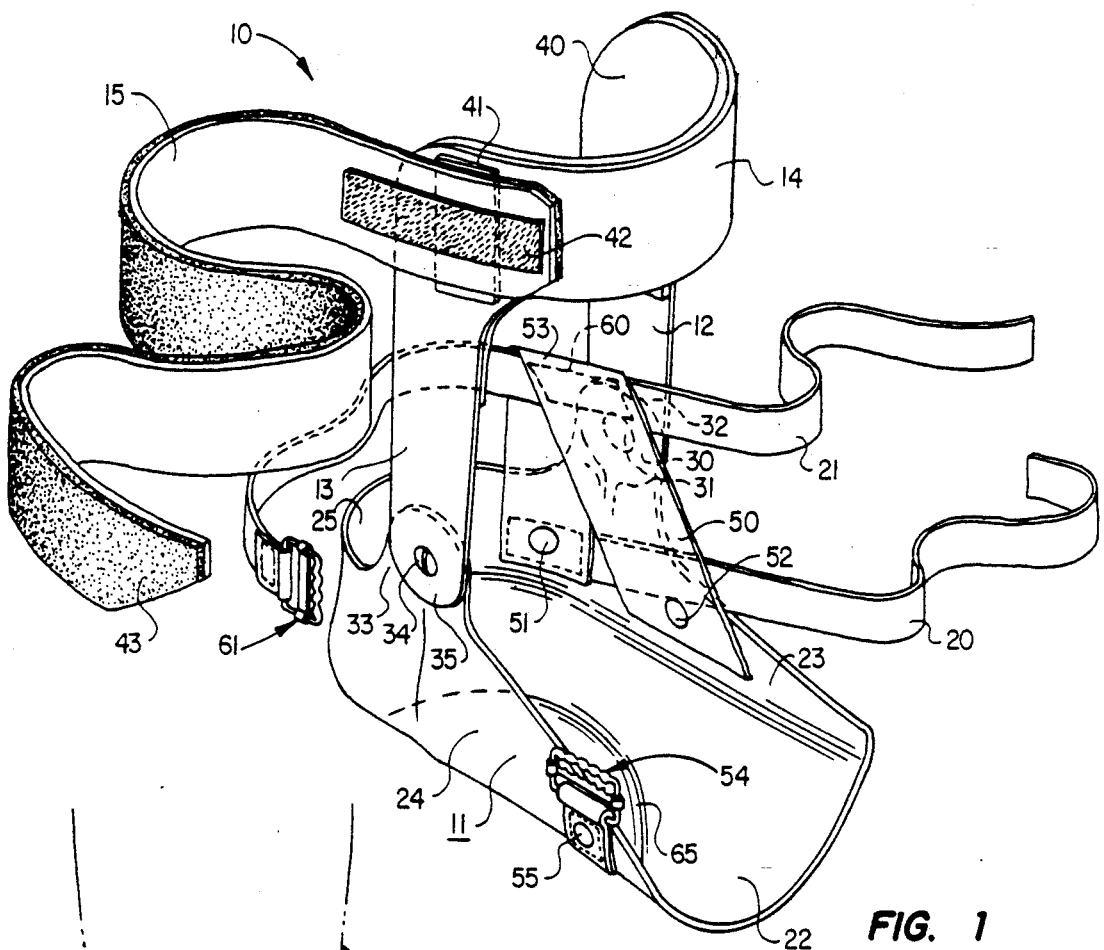
FIG. 1 is a view in perspective of preferred embodiment ankle brace of the invention designed for a left foot to protect against a lateral ankle sprain.

Referring to FIG. 1, an ankle brace 10 constructed in accordance with the invention includes a foot support shell 11, lateral and medial uprights 12 and 13, an anterior band 14, an anterior band strap 15 that wraps circumferentially about the posterior portion of the leg and the anterior band strap, a foot strap 20, and an ankle strap 21. The foot of the wearer rests in the shell 11 with the uprights 12 and 13 extending upwardly along the lateral and medial sides of the ankle and leg of the wearer with the anterior band 14 positioned across the front of the leg above the ankle over the tibia crest. The anterior band 14 is held securely on the tibia crest by the anterior band strap 15 wrapping around the posterior portion of the leg. The foot strap 20 is secured from the lateral side of the foot inside of the lateral side of the shell across the top of the foot anchored to the foot shell on the medial side toward the forward portion of the foot. The ankle strap is secured around the ankle from interior of the lateral upright 12 above the wearer's ankle joint with the ends of the ankle strap connected together on the medial side of the ankle joint, outwardly of the medial upright 13. The anterior band provides support to the device resting snugly against the tibia crest rather than against the fleshy part of the leg area behind the tibia crest as in prior art devices. The foot and ankle straps hold the ankle snugly in the foot shell and against the medial upright to minimize strain of the lateral compartment ligaments. The device primarily protects the lateral compartment ligaments which prevent inversion of the ankle joint.

In more specific detail, as shown in FIG. 1, the foot shell 11 is an integral molded member formed of a thin thermoplastic material which may be fabricated of a General Electric Corporation product sold under the trademark AZDEL. The foot shell has a foot plate 22 a lateral sidewall 23, a medial sidewall 24, and a rounded posterior wall 25 which joins with the sidewalls encircling the heel of the wearer. The lateral sidewall 23 has an upwardly curved hinge portion 30 which is attached by a suitable screw or brad 31 to the inside face of the lower end portion 32 of the lateral upright 12 providing a hinged connection between the lateral sidewall 23 and the lateral upright 12. Similarly, the medial sidewall 24 has an upwardly extended rounded hinged portion 33 which is attached by a suitable brad or screw 34 to a lower end hinge portion 35 of the medial upright 13 providing a hinged connection between the medial sidewall 24 and the medial upright 13.

As seen in FIG. 1, the anterior band 14 is formed integral with upper end portions of the lateral and medial uprights 12 and 13 in a curved configuration extending forwardly of the uprights for fitting around the tibia crest of the wearer. The interior face of the anterior band 14 is provided with a soft padding layer 40 formed of a suitable material such as a plastic foam or rubber. A latch panel 41 is cemented along the outer face of the upper end portion of the medial upright 13. The panel 41 has an external surface of a hook material or fastener sold under the trademark VELCRO. The strap 15 is formed of a suitable substantially non-elastic plastic web material provided with an inside face of VELCRO fastener material for attachment to the panel 41. The outer face of the strap 15 along one end portion has a longitudinally extending panel 42 cemented to the outer face of the strap and provided with an outer surface of a VELCRO fastener material so that the free end of the strap 15 when wrapped about the leg of a wearer and the front face of the anterior band 14 attaches to itself along the free end 43 of the strap to the VELCRO fastener panel 42 as seen in FIG. 2.

Referring again to FIG. 1, an ankle strap restrainer loop 50 is secured at opposite ends in spaced relation along the inside face of the lateral sidewall 23 by a first rear brad or screw 51 and a second forward brad or screw 52. The strap 50 is formed of a flexible but essentially non-elastic webbing formed of any suitable material. A central portion of the strap 50 is bent in the form of a loop 53 positioned generally in the vicinity and slightly above the hinge connection between the lateral upright 12 and the lateral sidewall 23. One end of the foot strap 20 is attached with an end of the strap 50 to the inside face of the sidewall 23 by the brad 51. The opposite free end of the foot strap is attachable to the medial sidewall 24 by a buckle assembly 54 attached by a brad 55 to the outside face of a forward portion of the medial sidewall 24. The ankle strap 21 is disposed along a central portion of the strap within and attached to, as by sewing at 60, the loop portion 53 of the strap 50. One of the free ends of the ankle strap 21 is provided with a buckle assembly 61 sized to attach with the opposite free end of the ankle strap 21. The straps 20 and 21 are formed of the same webbing material as the strap 50.

If desired, a scaphoid pad 65 is secured in the foot shell 11 along the foot plate and medial sidewall to provide an arch support and packing for supporting the ankle complex.

Figure 2:
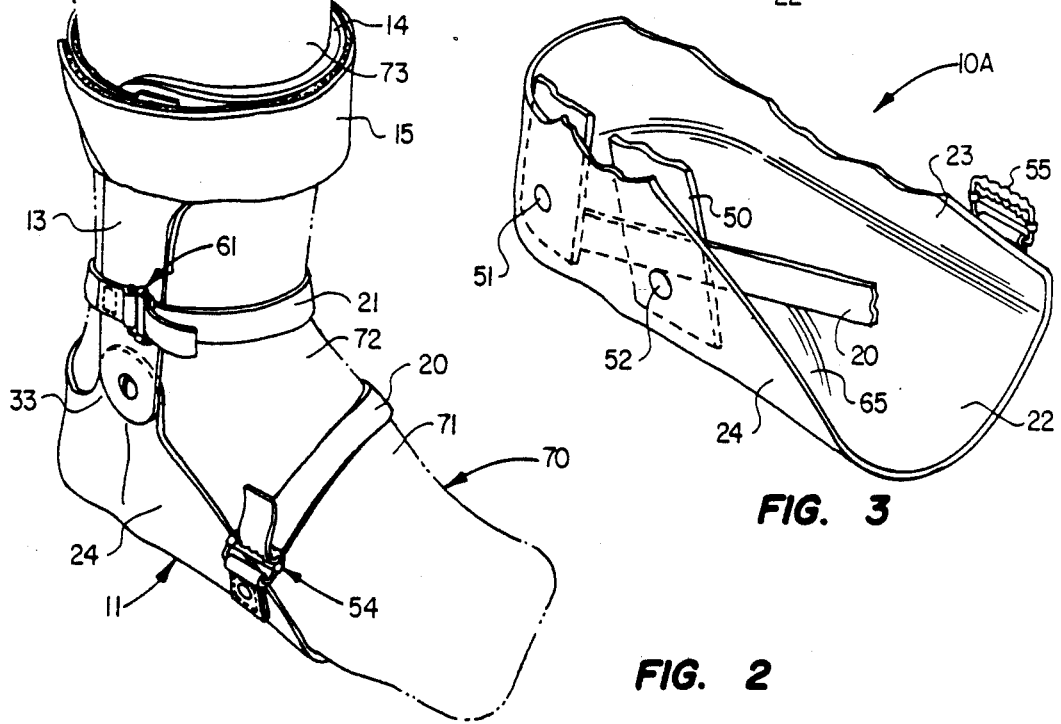
FIG. 2 is a view in perspective of the ankle brace of the invention as it is worn on a left foot.

The ankle brace 10 is worn on the foot and ankle and lower leg of a wearer as illustrated in FIG. 2. The foot 70 of the wearer rests in the foot plate 11 with the foot plate extending under the foot to the general vicinity behind the metatarsal head, along the bottom of the foot to the area of the heel, and upwardly around the heel and the medial and lateral sides of the foot as illustrated. The hinge area 33 of the sidewall 24 is positioned essentially along the medial melleoli of the wearer, as shown, while the lateral hinge portion of the sidewall 23 similarly is positioned along the lateral melleoli of the wearer, not illustrated. The foot strap 20 is connected along the free end portion of the strap to the buckle 54 and pulled securely at a forward angle across the top portion 71 of the foot 70. The ankle strap 21 is wrapped around the ankle 72 of the wearer above the lateral and medial melleoli with the free end of the strap being secured in the buckle 61 pulling the ankle strap 21 snugly around the ankle of the wearer outside of the upright 13 as illustrated in FIG. 2. With the anterior band 14 pressed snugly along the tibia crest 73 of the wearer, the anterior band strap 15 is wrapped around the leg of the wearer in the vicinity of the ankle and calf as seen in FIG. 2 with the free end of the strap 15 being wrapped upon itself and securely attached to the VELCRO panel 42. The strap 15 holds the anterior band 14 snugly along the tibia crest and the medial and lateral uprights 12 and 13 snugly along the medial and lateral sides of the ankle and calf portion of the leg of the wearer as shown. The combination of the foot strap 20, the ankle strap 21, along with the medial sidewall 24 and the medial upright 13, restrain the ankle of the wearer minimizing strain of the lateral compartment ligaments. The ankle brace is used with an outer shoe or boot and may be employed for therapeutic purposes with an existing ankle sprain or may be used for preventive purposes. The support provided by the anterior band 14 resting along the tibia crest and the cross bracing provided by the foot strap 20 and ankle strap 21 with the restrainer 50 provide a form of ankle bracing not believed to be present in prior art devices.

Figure 3:
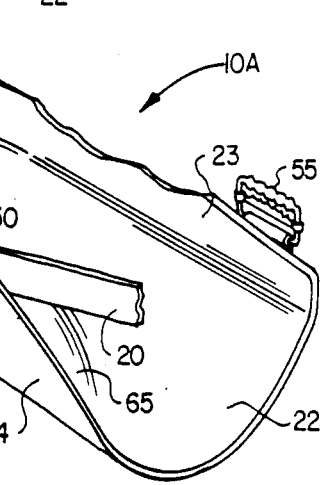
FIG. 3 is a fragmentary view in perspective showing the strap assembly of FIG. 1 attached to the opposite side of the foot shell to protect against a medial ankle sprain.

While FIGS. and 2 illustrate the ankle brace 10 for lateral ankle sprains, the brace design of the invention is equally applicable to medial sprains in the embodiment 10A shown in FIG. 3. As seen in FIG. 3, the foot strap 20 and the ankle strap 21 are secured with the opposite medial side of the foot shell. The looped strap 50 is connected by the brads 51 and 52 inside of the medial sidewall 24. The foot strap 20 is secured in the medial sidewall 24 by the brad 51. The buckle 55 is mounted on the lateral sidewall 23 as shown. The ankle strap attaches around the ankle of the wearer secured outside of the lateral upright 12. The ankle brace 10A thus functions as the brace 10 except to protect the medial compartment ligaments of the wearer.

While the ankle braces 10 and 10A are shown for a left foot and ankle, the brace designs are also applied to a right foot and ankle with the straps being attached to the lateral and medial sides of the foot shell as described and shown.

What is claimed is:

1. An ankle brace comprising:
   a foot support shell having a bottom plate, upright lateral and medial sidewalls, and a rounded posterior wall;
   a lateral upright member hinged at a first end to the upright lateral sidewall;
   a medial upright member hinged at a first end to the upright medial sidewall;
   a curved anterior band secured at opposite ends with the second ends of the lateral and medial uprights for positioning across the front of the leg of a wearer against the tibia crest;
   a leg strap securable around a leg of a wearer of the brace and the anterior band to hold the band against the tibia crest of the wearer;
   a foot strap secured along a first end to a rearward portion of the upright lateral sidewall and securable at a forward angle across the top of a foot of the wearer to a forward portion of the medial upright sidewall; and
   an ankle strap secured from a position above and inside of the lateral upright sidewall free of the lateral upright and connectable around the ankle of a wearer above the lateral and medial melleoli of the wearer outside of the medial upright member.

2. An ankle brace in accordance with claim 1 where the foot shell, medial and lateral uprights, and anterior band are formed of semi-rigid plastic and the straps are formed of a fabric material.

3. An ankle brace in accordance with claim 2 wherein the lateral and medial upright members are formed integral with the anterior band.

4. An ankle brace in accordance with claim 3 including an upwardly extending looped restrainer strap connected in spaced relation at opposite ends to the lateral sidewall and the ankle strap extends through a looped portion of the restrainer strap.

5. An ankle brace in accordance with claim 4 where the foot strap and the looped restrainer strap are secured to the inside face of the lateral sidewall.

6. An ankle brace in accordance with claim 5 where the hinged connection between the lateral and the medial sidewalls and the upright members are substantially in alignment with the lateral and medial melleoli of a wearer.

7. An ankle brace in accordance with claim 6 where the foot shell, the upright members, and the anterior band are of a molded semi-rigid plastic and the straps are of a fabric.

8. An ankle brace in accordance with claim 7 where the foot and ankle straps each include a buckle for securing the straps around the foot and ankle of a wearer and the leg strap includes hooked fabric attachment means.

9. An ankle brace comprising:
   a foot shell;
   lateral and medial upright members secured by hinge connections to opposite sides of the foot shell substantially at the lateral and medial melleoli of a wearer;
   an anterior curved band secured between the upper end portions of the upright members positioned to rest across the tibia crest of a wearer;
   means for releasably securing the anterior band across the front of a leg of a wearer against the tibia crest;
   a foot strap secured to a first side of the foot shell near the heel thereof and securable at a forward angle across the top of the foot of a wearer to the opposite second side of and toward the front of the foot shell; and an ankle strap secured inside and above the first side of the foot shell and inside and free of the upright member on the first side of the foot shell and connectable around the ankle of a wearer and the upright member on the second side of the foot shell.

10. An ankle brace according to claim 9 where the first side of the foot shell is the lateral side and the second side is the medial side.

11. An ankle brace according to claim 9 where the first side of the foot shell is the medial side and the second side is the lateral side.

12. An ankle brace comprising
a molded plastic foot shell including a foot plate, integral upright lateral and medial sidewalls, and a curved posterior wall connecting with the sidewalls, each of the sidewalls having an upwardly curved hinge portion;

a molded plastic lateral upright member hinged at a lower end with the hinge portion of the upright lateral sidewall;

a molded plastic medial upright member hinged along a lower end portion with the hinge portion of the upright medial sidewall;

a molded plastic curved anterior band formed integral with the lateral and medial upright members connecting upper end portions of the members, the anterior band being shaped and positioned to rest across the tibia crest of a wearer;

means on the outer face of one end portion of the anterior band for connection of a leg strap;

a leg strap having means along one end portion for connection with said connector means on the anterior band and adapted to wrap around the leg of the wearer and the anterior band securing the opposite end of the leg strap to means along the first end of the leg band for holding the anterior band on the leg of a wearer against the tibia crest of the wearer;

a looped restrainer strap secured in spaced relation along opposite ends to the inner face of a first of the sidewalls of the foot shell, one end of the looped strap being secured near the posterior wall of the foot shell and the other end of the looped strap being secured along a mid-portion of the first sidewall, the upper loop portion of the looped strap being located above the hinged connection between the upright member the first sidewall;

a foot strap secured along a first end to the internal surface of the first sidewall at the connection of the rearward portion of the looped strap with the first sidewall, the foot strap being extendable at a forward angle across the top of a foot of a wearer and securable to the opposite second of the sidewalls along a front portion of the sidewall;

a buckle on the second sidewall for connection of the foot strap;

an ankle strap extending through and secured along a central portion in the loop portion of the looped strap and extendable around an ankle of the wearer above the medial and lateral melleoli of the wearer; and a buckle on one end of the ankle strap for securing the ankle strap together around the ankle of the wearer outside of the upright member hinged to the second sidewall.

13. An ankle brace according to claim 12 Where the first sidewall is the lateral sidewall and the second sidewall is the medial sidewall.

14. An ankle brace according to claim 12 where the first sidewall is the medial sidewall and the second sidewall is the lateral sidewall.

15. An ankle brace comprising:
a foot support shell having a bottom plate, upright lateral and medial sidewalls, and a rounded posterior wall;

a lateral upright member hinged at a first end to the upright lateral sidewall;

a medial upright member hinged at a first end to the upright medial sidewall;

a curved anterior band secured at opposite ends with the second ends of the lateral and medial uprights for positioning across the front of the leg of a wearer against the tibia crest;

a leg strap securable around the posterior portion of the leg of a wearer of the brace and the anterior band to hold the band against the tibia crest of the wearer;

a foot strap secured along a first end to a rearward portion of the upright medial sidewall and securable at a forward angle across the top of a foot of the wearer to a forward portion of the lateral upright sidewall; and an ankle strap secured from above, and inside of the medial upright sidewall and inside and free of the medial upright and connectable around the ankle of a wearer above the lateral and medial melleoli of the wearer outside of the lateral upright member.

16. An ankle brace in accordance with claim 15 where the foot shell, medial and lateral uprights, and anterior band are formed of semi-rigid plastic and the straps are formed of a fabric material.

17. An ankle brace in accordance with claim 16 wherein the lateral and medial upright members are formed integral with the anterior band.

18. An ankle brace in accordance with claim 17 including an upwardly extending looped restrainer strap connected at opposite ends in spaced relation to the upright medial sidewall and the ankle strap extends through a looped portion of the restrainer strap.

19. An ankle brace in accordance with claim 18 where the foot strap and the looped restrainer strap are secured to the inside face of the upright medial sidewall.

20. An ankle brace in accordance with claim 19 where the hinged connection between the upright lateral and the upright medial sidewalls and the upright members are substantially in alignment with the lateral and medial melleoli of a wearer.

21. An ankle brace in accordance with claim 19 where the foot shell, the upright members, and the anterior band are of a molded semi-rigid plastic and the straps are of a fabric.

22. An ankle brace in accordance With claim 21 where the foot and ankle straps each include a buckle for securing the straps around the foot and ankle of a wearer and the leg strap includes hooked fabric attachment means.

23. An ankle brace according to claim 9 including a scaphoid pad on the foot shell toward the medial sidewall.

24. An ankle brace according to claim 12 including a scaphoid pad on the foot shell toward the medial sidewall.

* * * * *